United States Patent [19]

Miller et al.

[11] Patent Number: 4,801,865

[45] Date of Patent: Jan. 31, 1989

[54] MOISTURE SENSOR PROBE WITH AT LEAST TWO GROUPS OF RESISTIVE ARRAYS

[75] Inventors: Ralph W. Miller, Encinitas; Kent O'Brien, San Diego, both of Calif.

[73] Assignee: California Sensor Corporation, Carlsbad, Calif.

[21] Appl. No.: 144,957

[22] Filed: Jan. 19, 1988

[51] Int. Cl.⁴ .......................................... G01R 27/02
[52] U.S. Cl. .......................... 324/65 R; 324/65 P; 340/602; 73/336.5
[58] Field of Search ............... 324/65 R, 65 P; 340/602; 338/34; 73/336.5; 361/78

[56] References Cited

U.S. PATENT DOCUMENTS

| | | | |
|---|---|---|---|
| 2,611,643 | 9/1952 | Higgins | 324/65 R |
| 2,636,962 | 2/1953 | Bouyoucos | 324/65 R |
| 2,721,101 | 10/1955 | Richard, Jr. | 324/65 R |
| 2,768,028 | 10/1956 | Robinson | 324/65 R |
| 2,781,228 | 2/1957 | Anderson | 324/65 R |
| 2,812,976 | 11/1957 | Hasenkamp | 324/65 R |
| 2,985,827 | 5/1961 | Hasenkamp | 324/65 R |
| 3,037,704 | 6/1962 | Kinigsberg et al. | 239/63 |
| 3,182,914 | 5/1965 | Hosier | 324/65 R |
| 3,195,816 | 7/1965 | Mercer | 324/65 R |
| 3,631,337 | 12/1971 | MacKinney | 324/65 R |
| 4,522,060 | 6/1985 | Murata et al. | 324/65 R |
| 4,652,811 | 3/1987 | Kwiat et al. | 324/65 P |
| 4,734,554 | 3/1988 | Tateda et al. | 73/336.5 |

Primary Examiner—Reinhard J. Eisenzopf
Assistant Examiner—Maura Regan
Attorney, Agent, or Firm—Baker, Maxham & Jester

[57] ABSTRACT

A probe for sensing the moisture content in a porous medium such as soil. The probe includes an array of a multiplicity of conductors and resistors formed on a substrate, with contact pins or electrodes connected to one end of each resistor, typically extending outwardly from the substrate. The resistor array is preferably divided into at least two groups, providing a separate output for each group. An appropriate voltage source and indicator means are connected to the resistor array in a circuit to provide indication of soil moisture. The transfer characteristic of the apparatus is such that the probe has improved sensitivity in the area of primary interest, that is at, between 80 and 100% of saturation.

9 Claims, 2 Drawing Sheets

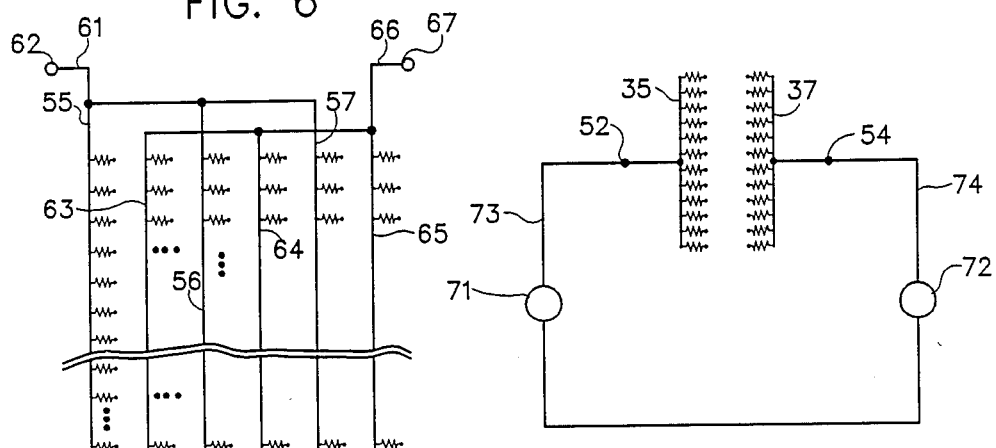
FIG. 6
FIG. 7
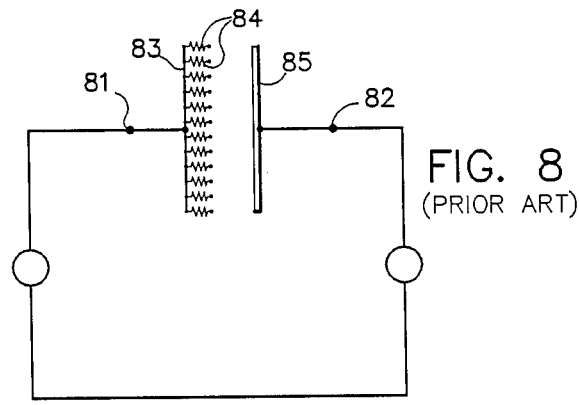
FIG. 8
(PRIOR ART)
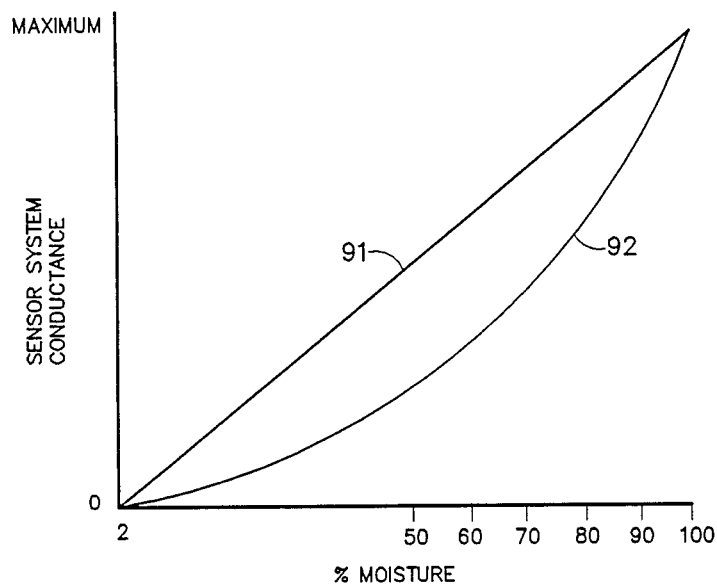
FIG. 9

4,801,865

MOISTURE SENSOR PROBE WITH AT LEAST TWO GROUPS OF RESISTIVE ARRAYS

FIELD OF THE INVENTION

This invention relates generally to moisture sensing devices and more particularly concerns a resistive moisture sensing probe with greatest sensitivity in the area of primary interest for landscape irrigation at between 80 and 100% of saturation, or 5 to 30 centibar.

BACKGROUND OF THE INVENTION

Many attempts have been made in the past to provide reliable systems for maintaining an optimum of moisture in the soil for growing crops such as lawns, flowers, gardens and farm produce. Automatic systems are well known which operate on a predetermined time sequence which may be adjusted for seasonal and atmospheric conditions. Some systems utilize moisture sensing probes inserted into the soil for sensing the moisture content. However, a number of drawbacks have been encountered in known buried sensing probes, one of them being insufficient sensitivity, especially at high saturation levels. For growing turf, it is commonly desired to have soil moisture at between 80 and 100% of saturation and that is where moisture probe sensitivity should ideally be optimum. Another problem with prior art moisture sensing probes is that they tend to have a relatively short useful life, being subject to corrosion.

Various configurations of moisture sensing probes have been employed. Some of these are configured as a pair of probes spaced apart in the soil where the system measures the conductivity between the probes. Another moisture sensor, as shown in U.S. Pat. No. 4,652,811, employs a group of resistors, each having a point contact, and a distributed electrode, the point contacts and the electrode being in contact with the soil being monitored. The transfer characteristic and thereby the sensitivity of this device is substantially the same whether the soil is dry or saturated.

Certain characteristics of the porous medium and the moisture therein give rise to some of the difficulties in measuring the moisture content. Damp mediums, such as soils, are electrolytic and are characterized mainly by a number of electrical parameters such as; electrical conductivity, electrical capacitance, and electrical inductance. These parameters vary with the characteristics of the medium. The main characteristics which influence these parameters are the medium's density, structural form, chemical composition and moisture content.

SUMMARY OF THE INVENTION

Broadly speaking, this invention provides an effective, long life moisture probe for porous media such as soil which, in the range of primary interest for turf, has significantly improved sensitivity.

Stainless steel or equivalent non-reactive contact pins are connected to leads on a printed circuit substrate and preferably to printed resistors. The pins provide point contacts after the circuitry surface is encapsulated for ambient protection. Both sides of the circuitry comprise the point contacts of the contact pins which are in contact with the medium being monitored. A voltage source and a signal indicator or control system complete the basic moisture sensor circuitry.

When moisture in the medium bridges two or more of the point contacts, the indicator reflects a current flow change which is indicative of increased moisture in the medium. The preferred embodiment includes a printed resistor connected to each contact pin.

BRIEF DESCRIPTION OF THE DRAWING

The objects, advantages and features of this invention will be more readily perceived from the following detailed description, when read in conjunction with the accompanying drawing, in which:

FIG. 6 is a schematic representation similar to FIG. 5 showing an alternative electrical connection embodiment;

FIG. 7 shows the sensor of FIGS. 5 or 6 connected in an electrical circuit;

FIG. 8 is a representation of the prior art presented similarly to FIG. 7; and

FIG. 9 is a graphical representation of the transfer characteristics of the circuit of FIG. 7 compared with the circuit of FIG. 8.

DESCRIPTION OF PREFERRED EMBODIMENTS

Figure 1:
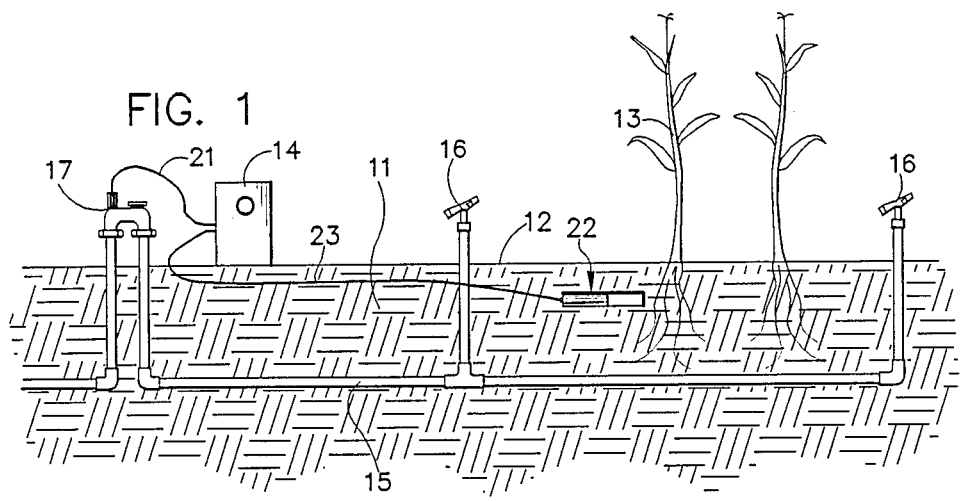
FIG. 1 is a schematic illustration of a portion of an irrigation system embodying the present invention.

With reference now to the drawing and more particularly to FIG. 1 thereof, the ground or soil is represented by reference numeral 11, having top surface 12 in which a desirable crop of plants 13 has been planted and is growing. The irrigation system comprises control unit 14, piping 15 and dripper or sprinkler units 16. Control valve 17 is representative of any suitable control valve system or valve arrangement, regulated by control units 14 through electrically conductive or pneumatic line 21. Moisture sensing probe 22 is located in the vicinity of the plants at a typical depth of 4 to 6 inches below surface 12 and remote from the control unit. Electrically conductive line 23 connects probe 22 with control unit 14.

In normal operation, the irrigation and control system of FIG. 1 would be calibrated so that when the soil is below desired moisture content, water is called for and control unit 14 opens valve arrangement 17 to apply water to the soil until the desired moisture content is reached and sensed by probe 22. At that time, the control unit would respond by sending a signal to valve means 17 and turning off the source of water to irrigation heads 16.

Figure 2:
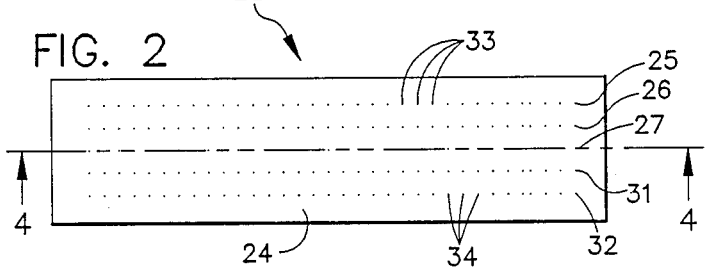
FIG. 2 is a front elevational view of the multiple contact array probe of the system of FIG. 1.

Moisture sensing probe 22 is shown in somewhat greater detail in FIG. 2. The probe comprises a body 24 which contains the printed circuitry and resistive elements shown in FIG. 3 which are encapsulated, typically by potting or by injection molding, for protection against the elements. Contact pins extend outwardly from one end of each resistive element forming rows 25, 26, 27, 31 and 32, ending in exposed contact points 33 and 34. Contact points 33 reside in row 25 and contact points 34 reside in row 32. The other three rows have similar numbers and configurations of contact points.

Figure 3:
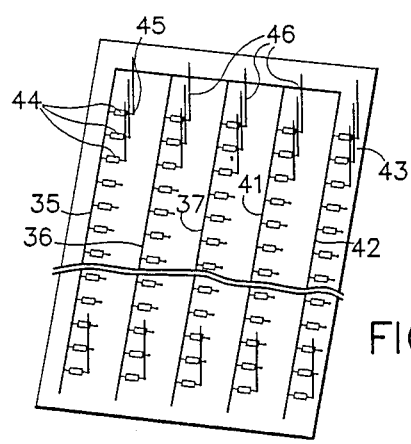
FIG. 3 is a perspective view of the rigid substrate on which the printed circuitry is formed and from which the contact ends extend.

In FIG. 3 printed conductive paths 35, 36, 37, 41 and 42 are printed on one surface of substantially rigid substrate 43. Also, printed on the substrate are resistors 44 connected to conductive path 35. Connected to each resistor 44 is a pad 45 to which a contact pin 46 (FIGS. 3 and 4) is connected by suitable means such as by welding, soldering, brazing or conductive adhesive. The surface of substrate 43 on which the resistor elements and contact paths are printed and to which contact pins 46 are mounted is then potted with potting material 47 to a predetermined depth. Then the protruding ends of pins 46 are cut off, leaving a relatively smooth surface of potting material with 0.020 inch diameter contact point cross section flush with that potting material surface.

Figure 4:
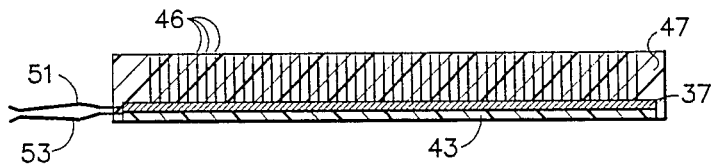
FIG. 4 is a sectional view taken along cutting plane 4—4 of FIG. 2.
Figure 5:
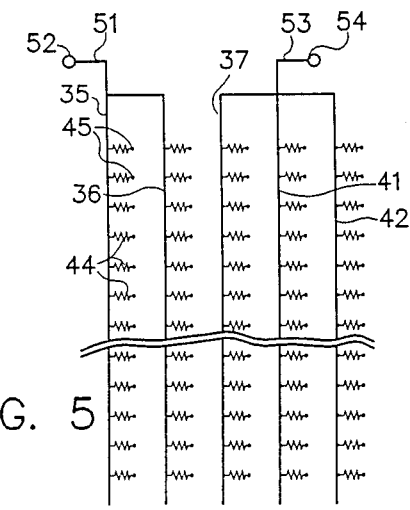
FIG. 5 is a schematic representation of the multiple contact resistance array on the substrate showing an example of the electrical connections and outputs.

FIG. 4 shows, in cross section of the probe of FIG. 2, the configuration of FIGS. 3 and 5. Substrate 43 supports circuitry, represented by conductive path 37, and upright parallel contact pins 46.

One possible circuit connecting arrangement for the groups of parallel connected resistors in the array is shown in FIG. 5. Conductive paths 35 and 36 with their associated resistors are connected together in parallel and to output line 51 connected to output terminal 52. Conductive paths 37, 41 and 42 are parallel interconnected by means of line 53 and to output terminal 54.

An alternative embodiment is shown in FIG. 6. In this embodiment printed circuit conductors 55, 56 and 57 are connected together in parallel to output line 61 and to output terminal 62. Similarly, conductive paths 63, 64 and 65 are parallel connected to output line 66 and to output terminal 67. As in the embodiment of FIG. 5, each conductive path is connected to a plurality of parallel connected resistors printed on the same substrate.

A simple sensor circuit selectively embodying the arrangements of FIG. 5 or FIG. 6 is shown in FIG. 7. The conductive paths to which the multiplicity of resistors are connected, which are connected to output terminal 52, is represented by reference numeral 35. Similarly, reference numeral 37 represents the groups of resistors connected to output terminal 54. While, any convenient arrangement may be used, it is possible that only the conductive paths, and resistors and contact pins are in moisture sensing probe 22 and that voltage source 71 and signal indicator 72 are located in control unit 14. Line 23 shown in FIG. 1 would in that case comprise conductors 73 and 74 from output terminals 52 and 54.

For reference purposes, a prior art circuit having the general arrangement of FIG. 7 as shown in FIG. 8. In this circuit, from U.S. Pat. No. 4,652,811, output terminal 81 is connected to conductive path 83 and a plurality of resistors 84, similar to the arrangement of FIG. 7. However, output terminal 82 is connected to a single distributed or large conductor 85, the rest of the circuitry being the same.

The electrical effect of the circuit difference between FIG. 7 and FIG. 8 is shown in the graph of FIG. 9. Curve 91 shows sensor system conductance versus percentage moisture for the prior art configuration of FIG. 8. Note that this curve is linear and that at 100% moisture or saturation, the conductance of the sensor system reaches maximum. Note also that the sensor sensitivity does not vary throughout the range of conductance and moisture. Curve 92 on the other hand shows the transfer characteristic of the probe, indicating that it has much greater sensitivity in the area where the moisture is 80–100% of saturation, and is especially sensitive above 90% saturation. Since, as stated previously, it is desired to have the moisture level for turf in the region above 80% saturation, by having the slope of curve 92 at approximately a 2:1 ratio with respect to the slope of curve 91, it is easily appreciated that the sensitivity of the moisture sensor probe is improved at approximately the same ratio over linear curve 91.

It has been found that the embodiments of both FIGS. 5 and 6 give improved sensitivity in the near saturation region but that the interweaved circuitry of FIG. 6 is preferred. It makes little difference from the standpoint of manufacturing costs.

The reason for improvement of this device over the prior art can be easily understood by a few observed facts. In the prior art as shown in FIG. 8, a number of small electrodes contact the earth, each having a high valued resistor electrically in series to one common terminal 81. The second electrode 85 has a large surface area which contacts the ground water in the earth. It then connects to the second output terminal 82 and on to the subsequent conductance measuring equipment. This type of device assembly exhibits an increasing conductance with water content. The details by which water is stored in soil need not be invoked to understand two simple facts from the prior art.

The first fact is that the large electrode is continually in contact with water in the soil independent of the density of the ground water in the porous soil medium. If a probability factor were assigned to the large probe making contact with ground water then its value would be unity signifying continual continuity. On the other hand not all of the small electrodes are in apparent electrical contact with ground water until the soil is totally saturated. This then is the second fact repeated for emphasis that not all of the small electrodes are in apparent electrical contact with ground water. The probability of the small electrodes making contact is less than one. The prior art device therefore exhibits increased conductance with increased ground water content and this behavior is strongly related to the probability of the small electrodes making electrical contact with ground water and little influenced by the large area contact electrode.

The improved device draws upon these basic observations and provides a second set of small electrodes to replace the large area electrode, as shown in FIG. 7. Now both sets of electrodes have about equal probabilities for contacting ground water in the soil medium. A product of probability function applies to this case. Thus a square law of increasing conductance with ground water is an approximate relationship for the improved device. Taking an example, if the prior art device exhibited 90% conductance, then the improved device having both groups made of small electrodes exhibits 81% normalized conductance. However, at 100% saturation both would indicate full value. The rate of change or the sensitivity is thus substantially improved for the new moisture sensing device. A transfer characteristic for the conductance versus moisture content of a somewhat more detailed model of the same problem which takes spatial features into account is shown in FIG. 9. The strong square law features are noted in this characteristic.

The measurement of electrical conductivity of the pin array is a measure of the moisture content of the earth.

Although not an absolute measurement because of the many variations of the soil, for any given ground location, tests have shown significant consistency of measurement, thus making it practical to observe moisture and calibrate the sensor in terms for conductivity. Thereafter the calibrated conductivity can be used to indicate the moisture content to a practical degree as would be necessary for plant and grass watering control. This transfer characteristic for the FIG. 8 structure is depicted as curve 91 in FIG. 9, showing the conductivity to vary linearly with moisture content change.

The prior art construction represented by FIG. 8 has several disadvantages which limits its use and ease of manufacturer. Constructing electrode 85 in the same body as the pin electrodes connected to resistors 84 may be difficult or economically impractical. Additionally, the common electrode may be separated by some distance or in a different plane from the contact pins and thereby not continuously in contact with the ground water. This is particularly troublesome for soil which shifts or moves in response to varying degrees of moisture. Under such conditions the calibration may change or be unreliable. Another problem is that the porosity and composition of some types of soil may not allow continual contact with all interstitial water pores so that some of the pin electrodes would not contribute to conduction and thereby render the sensor even less sensitive or variable in calibration. Additionally, resistors 84 may be individual component resistor rather than the printed resistors of the present invention. The point contacts may then be the copper resistor leads, leading to a corrosion problem, or it would be necessary to form an interface between the copper leads and the point contacts.

The disadvantages mentioned above are overcome by the configuration of FIGS. 5-7 where a single pin array is separated into two parts. A portion (which may be half) of the array terminates in one electrode and the remaining resistors and contact pins terminate in the other electrode. FIG. 5 shows two adjacent rows or groups of resistors and contact pins connected to output terminal 52 and the remaining three rows or groups of resistors and pins, corresponding with the configuration of FIG. 2, connected to output terminal 54. FIG. 6 shows alternating groups of parallel connected resistors and contact pins connected alternatively to output terminals 62 and 67. There are, in this case, three parallel groups of resistors and contact pins connected to each output terminal. Of course, the interweaving configuration could be as easily employed with an odd number of groups of resistors and contact pins as is shown in FIG. 5. Thus, in contrast with the prior art of FIG. 8, all exposed electrodes are contact pins of the same type, in the same plane, and are physically close, typically about 2 mm between pins in a row and 4-5 mm between rows. With the configuration of FIG. 6, with alternating columns used for opposing output electrodes, even small interstitial water pores or packets are much more favorably disposed to contribute to the conductivity of the array. Essentially, all of the electrode elements in the FIG. 7 configuration are used gainfully. Also, by being in the same mappable surface, reliable contact with the soil and interstitial water pores can be maintained with small soil movements or strain. This contributes to the stability of the output of the sensor.

It is important to realize that interstitial pore water, as it contacts the pin electrodes, acts as a switch for electrical conduction. When the term "conductivity" is used with respect to this invention, it is referring not to the degree of the conductivity of the soil itself but to the conductivity of the combination of the probe elements and the soil, thereby accounting for the extremely low conductivity of dry soil and the relatively shorted or high conductivity characteristic of saturated or wet soil. Thus, as water in the pores of the soil bridges any two contact pins, it acts as a switch. If the contact pins are in the same parallel combination, it merely completes a parallel connection with commensurate change in the value of the combined resistance. If it is between the contact pins connected with the opposite output terminals, it provides one portion of circuit completion between voltage source 71 and signal indicator 72. It is this combination of electrode interconnection through the resistors which gives rise to the improved transfer characteristic shown by curve 92 in FIG. 9.

In practical terms, in normal soil water first coats soil particles and then as the percentage of moisture increases, fills the pores or interstices between these particles. The moisture probe of the present invention measures the density of the pores that are full of water. Each contact point for each electrode touches or is adjacent to a pore. In this system, conductivity is cumulative so that the more points that are in contact with water, the greater the conductivity. Again, note that this characteristic does not depend upon soil conductivity. The probe of this invention is insensitive to the specific conductivity of the soil involved. This device only measures the number of contact points which are wetted where each point acts as a switch.

Installation of the moisture sensing probe is relatively simple. After the probe is inserted into the ground, 4 to 6 inches below the surface, the soil is heavily watered to compact it around the probe. At that time the probe is prepared to perform its desired function over a long period of time.

Examples of the structural components include the fact that the substrate is preferably a rigid, non-conductive material. It may be ceramic or it could be an organic polymer or other suitable material. However, it is important to realize that rigidity of the substrate is not a requirement for the invention to function properly. It is also possible that portions of the substrate itself can be conductive, but the electrical circuitry needs to be electrically isolated therefrom. The contact pins are preferably stainless steel which easily interfaces with the pads formed at the free end of the printed resistors as shown in FIG. 3. Note that discrete resistors normally have copper electrodes and these can easily corrode. The moisture sensing probe according to this invention, with printed resistors, is substantially less expensive to manufacture than would be a similar probe formed with discrete resistors. As an alternative to stainless steel, the electrodes could be a carbon based pin or any other kind of corrosion resistant conductive element. It is also significant that the moisture sensing probe of this invention is not sensitive to salinity in the soil. This is consistent with the fact that the conductivity of the system does not depend upon the relative conductivity of the soil.

Quantifying the relative resistance of dry and wet soil compared with the printed circuit resistor values will aid in understanding the electrical characteristics of the invention and the circuitry. In dry soil, the paths between two contact pins is hundreds of megohms whereas when there is a water path between them in the soil, the resistance is only a few thousand ohms. Additionally, each printed circuit resistor is assumed to be in the range of 10 megohms but that is not a critical number. Thus, while each wetted path is a few thousand ohms, it is equivalent to a short circuit compared with the multiple megohm paths of the resistor or of dry soil. This supports the statement that the conductivity of the soil itself is not relevant to the invention. The conductivity of the system, which concludes the sensor and the soil, is a function of how many pins are in contact with water.

The voltage source is contemplated to be an alternating square wave varying between $-2.5$ volts and $+2.5$ volts. Signal indicator 72 may be a current meter or any other means to show signals. One example is a synchronously demodulated meter which is not sensitive to spurious signals and changes sign when the applied voltage sign changes. The indicator could be a digital meter, a CRT, a strip chart recorder or any other type of suitable indicator device. Instead of using an indicator, the moisture sensor probe could be coupled directly in an irrigation control system, as shown in FIG. 1. It is contemplated that the sensor probe will employ at least about 100 contact pins, but a higher number improves resolution.

The above description relates to a configuration with all of the printed conductors and resistors being closely adjacent on a single surface of the substrate. However, it is possible that the resistors could be located anywhere on the substrate, even at different levels. For curve 92 of FIG. 9 to apply, with the commensurate advantages, it is only necessary that the exposed contact points be closely adjacent so that even relatively small water packets will bridge at least two such contact points. Further, the tops of the pins or contact points need not be planar in the completed embodiment. Also groups of the resistors and pins could be in a single plane but not be parallel.

In view of the above description, it is likely that modifications and improvements will occur to those skilled in the art which are within the scope of the appended claims.

What is claimed is:

1. A probe for sensing moisture content in a porous medium, said probe comprising:
   a substrate;
   an array of at least a first and a second group of resistors formed on said substrate, there being a multiplicity of resistors in each said group;
   first conductor means formed on said substrate interconnecting one end of all of said multiplicity of resistors in said first group together in a partial parallel configuration;
   first output terminal means connected to said first conductor means;
   a first electrode connected to the other end of each said resistor in said first group of resistors;
   second conductor means formed on said substrate interconnecting on end of all of said multiplicity of resistors in said second group together in a partial parallel configuration;
   second output terminal means connected to said second conductor means;
   a second electrode connected to the other end of each said resistor in said second group of resistors, said first and second electrodes being adjacent and electrically isolated within said probe; and
   encapsulating material sealing said resistors, conductors and electrodes, said encapsulating material protecting all but the ends of each said first and second electrode from the environment.

2. The probe recited in claim 1, wherein said first and second output terminal means are adapted to be selectively connected to circuitry comprising a voltage source and indicator means, whereby said probe, pursuant to voltage applied thereto, produces output signals representative of moisture content in the medium, the indicator means providing moisture content indication in response to the output signals.

3. The probe recited in claim 1, wherein said first and second output terminal means are adapted to be selectively connected to circuitry comprising a voltage source and an irrigation control system, whereby said probe, pursuant to voltage applied thereto, produces output signals representative of moisture content in the medium, said control system controlling the amount of fluid applied to the medium in response to the output signals.

4. The probe recited in claim 1, wherein at least two groups of resistors and first electrodes are connected to said first output terminal means.

5. The probe recited in claim 1, wherein:
   at least two groups of resistors and first electrodes are connected to said first output terminal means; and
   at least two groups of resistors and second electrodes are connected to said second output terminal means.

6. The probe recited in claim 5, wherein said first group of resistors and first electrodes are electrically isolated and physically closely adjacent said second group of resistors and second electrodes.

7. The probe recited in claim 6, wherein said first group of first electrodes is arranged in physically alternating fashion with said second group of second electrodes.

8. A method for measuring moisture content of a porous medium, said method comprising the steps of:
   placing a multiplicity of contact points in contact with the medium, said contact points being arranged in at least two groups;
   applying a voltage to said contact points;
   inserting a predetermined electrical resistance between each of said contact points and the voltage source, at least one group of said contact points being spaced from and electrically separate from the other groups; and
   determining the moisture content in the medium as a function of the number of said contact points being wetted and being connected through the moisture to at least one other of said contact points.

9. The method recited in claim 8, wherein the resistance value between two contact points unconnected by moisture and the resistance value of each predetermined electrical resistance is several higher than is the resistance value between two contact points connected by moisture.

* * * * *